United States Patent [19]

Kiyota et al.

[11] Patent Number: 5,453,076
[45] Date of Patent: Sep. 26, 1995

[54] INTERNAL CARDIAC ASSIST APPARATUS

[76] Inventors: Yoshiharu Kiyota, 3-43-107, Chokojiminami 2-chome, Toyonaka-shi, Osaka 560; Yasuhiko Shimizu, 39-676, Kohataogurayama, Uji-shi, Kyoto 611, both of Japan

[21] Appl. No.: 142,341
[22] PCT Filed: Apr. 15, 1993
[86] PCT No.: PCT/JP93/00481
  § 371 Date: Nov. 18, 1993
  § 102(e) Date: Nov. 18, 1993
[87] PCT Pub. No.: WO92/20861
  PCT Pub. Date: Oct. 28, 1993

[30] Foreign Application Priority Data

Apr. 17, 1992 [JP] Japan ................................ 4-97725

[51] Int. Cl.⁶ ................................................. A61N 1/362
[52] U.S. Cl. .................................................. 600/18; 604/96
[58] Field of Search ........................... 600/16–18; 623/3; 604/96–99

[56] References Cited

U.S. PATENT DOCUMENTS

| | | | |
|---|---|---|---|
| 4,546,759 | 10/1985 | Solar | 600/18 |
| 4,576,142 | 3/1986 | Schiff | 600/18 |
| 4,943,275 | 7/1990 | Stricker . | |
| 4,968,300 | 11/1990 | Moutafis et al. . | |
| 5,090,957 | 2/1992 | Moutafis et al. . | |
| 5,116,305 | 5/1992 | Milder et al. | 600/18 |

FOREIGN PATENT DOCUMENTS

| | | |
|---|---|---|
| 57-119763 | 7/1982 | Japan . |
| 62-139501 | 9/1987 | Japan . |
| 63-286168 | 11/1988 | Japan . |
| 1-178053 | 12/1989 | Japan . |
| 2-297381 | 7/1990 | Japan . |

OTHER PUBLICATIONS

Biventicular Cardiac Assistance Energized by Suction Actuated Recoil of a Single Constricting Rubber Ventricle, Kolobow et al vol. XI, Trans. Amer. Soc. Artif. Int. Organs, 1965. pp. 57–64.

Synchronization of Direct Mechanical Ventricular Assistance to the Electrocardiogram, Peter Schiff et al, Trans. Amer. Soc. Int. Organs, 1969, pp. 424–429.

Programmable Pneumatic Generator for Manipulation of Intrathoracic Pressure, H. Halperin, et al, IEEE Transactions on Biomedical Engineering, vol. BME–34, No. 9, Sep., 1987, pp. 738–742.

Rhythmic Intrpericardial Tamponade: A Method of Assisting or Maintaining Circulation, Norman Rosenberg, et al, pp. 980–989.

The Association of Aberrant Renal Arteries and Systemic Hyupertension, John Derrick, et al, pp. 907–.

Direct Mechanical Ventricular Actuation for Cardiac Arrest in Humans, A Clinical Feasibility Trial, M. Anstadt et al, (List continued on next page.)

Primary Examiner—Kyle L. Howell
Assistant Examiner—John P. Lacyk
Attorney, Agent, or Firm—Frishauf, Holtz, Goodman, Langer & Chick

[57] ABSTRACT

An internal cardiac assist apparatus includes a balloon 1 having a variable internal volume, and a tube 2 that feeds and discharges a gas within said balloon. One end of the tube 2 is sealed. The balloon is secured to the tube so that the balloon contains the tube for a prescribed length of the tube near the one end of said tube which is sealed. At least one hole 23 for feeding and discharge of the gas is provided in the lengthwise direction in a wall 22 of the portion of the tube that is contained in the balloon. The internal cardiac assist apparatus imposes less of a burden on serious coronary insufficiency patients (by not requiring thoracotomy or incision of the pericardium, and therefore having little effect on breathing and causing little pain), does not require the provision of a complicated gas feeding apparatus, and reliably assists cardiac contraction over a long period of time.

24 Claims, 9 Drawing Sheets

OTHER PUBLICATIONS

Mechanical Ventricular Actuation for Cardiac Arrest, pp. 86–92.

Prolonged Circulatory Support by Direct Mechanical Ventricular Assistance, G. Anstadt, et al, Trans. Amer. Soc. Artif. Int. Organs, 1966, pp. 72–79.

Rhythmic Intrapericardial Tamponade; A Method of Assisting or Maintaining, N. Rosenberg, et al, vol. 56, No. 5, Nov., 1964, pp. 980–988.

Studies in Experimental Mesenteric Venous Occlusion, The Experimental System and Its Parameters, H. Polk, Jr., American Journal of Surgery, vol. 108, Nov. 1964.

Alterations in Fibrinolysis and Coagulation Associated with Cardiopulmonary Bypass, J. Porter, et al, The U.S. Stoneware Corporation.

Mechanical Circulatory Assistance in the Treatment of Cardiac Failure, D. Goldfarb, Progress in Cardiovascular Disease, vol. XII, No. 3, Nov. 1969.

Mechanical Assistance to the Circulation: The Principle and the Methods, W. Kolff, et al, Progress in Cardiovascular Diseases, vol. XII, No. 3, Nov. 1969.

Vascular Responses to Intra–Arterial Diodrast and Urokon During Arteriography, R. Shaw, Harvard Medical School.

INTERNAL CARDIAC ASSIST APPARATUS

TECHNICAL FIELD

The present invention relates to an internal cardiac assist apparatus, and more particularly, to an internal cardiac assist apparatus used to assist the cardiac contraction of serious cardiac failure patients for a long period of time.

BACKGROUND OF THE INVENTION

Various apparatuses have been proposed that cyclically compress the heart (ventricles only) through the use of pressure changes of gases initially for the purpose of replacing open chest manual massage (directly massaging the heart by hand, a practice frequently used to resuscitate cardiac arrest patients) with machines, and then assisting the heart synchronous to heart beat following resumption of heart beat. The following provides a description of some typical examples of these apparatuses.

1) Apparatuses Using the Pericardium for Demonstrating Function

Examples of these apparatuses include an apparatus which feed a gas directly and cyclically into the pericardial cavity (using the pericardium as a balloon which can be inflated and deflated by feeding and discharging a gas thereinto) (refer to Adriano Bencini, et.al., Surgery, 1956, Vol. 39, No. 3, p. 375-); an apparatus in which a balloon is inserted into the pericardial cavity that can be inflated and deflated by feeding and discharging a gas into said balloon, that directly compresses the left ventricle with said balloon, and compresses the right ventricle by pinching the right ventricle between the left ventricle compressed with said balloon and the pericardium (the pericardium serves as a surface that reacts to the pressure resulting from inflation of said balloon) (a. an apparatus in which, although the balloon in this case only expands in the direction of compression of the left ventricle, with the portion that makes contact with the pericardium on the side of the left ventricle being lined with nylon mesh, the connection between said balloon and the device for feeding and discharging the gas is located at a single point on the surface of said balloon—refer to Gerald A. Jones, et.al., Dis. Chest, 1961, Vol. 9, p. 207-, and b. an apparatus is disclosed in which the inflation and deflation of said balloon can be synchronized with the heart beat—refer to Norman Rosenberg, et.al., Surgery, 1964, Vol. 56, No. 5, p. 980-); and, an apparatus in which balloons that can be inflated and deflated by feeding and discharging a gas thereinto are each sutured in position on the outer surface of the pericardium at locations geometrically corresponding to the left and right ventricles—refer to C. W. Hall, et.al., American Journal of Surgery, 1964, Vol. 108, p. 685-.

However, since these apparatuses result in excessive extension of the pericardium, there is the risk of causing its rupture. As these apparatuses are not even able to fulfill the objective of mechanical replacement of open chest manual massage, they have gradually fallen out of use (furthermore, as can be ascertained from their mode of use, these apparatuses require thoracotomy, and depending on the case, incision or puncture of the pericardium).

2) Apparatuses not Requiring Use of the Pericardium for Demonstrating Function

Apparatuses that attempt to solve the above-mentioned problems of the prior art are of a type referred to as apparatuses in which membrane member that can be expanded and contracted with the feeding and discharge of a gas into an inner space enclosed with said membrane member is arranged on the inner surface of a vessel able to contain both ventricles (said membrane member being respectively attached to said vessel entry and lower wall), and cyclical compression is applied to the heart by expanding and contracting said membrane member through the feeding and discharge of gas into the inner space enclosed with said membrane member with both ventricles suctioned and contained in said vessel (currently typically referred to as DMVA (direct mechanical ventricular actuation) (refer to Mark W. Wolcott et.al., Surgery, 1960, Vol. 48, No. 5, p. 903-; Theodor Kolobow et.al., Trans. Amer. Soc. Artif. Int. Organs Vol. XI, 1965, p. 57-; G. L. Anstadt et.al., Trans. Amer. Soc. Art if. Int. Organs Vol. XII, 1966, p. 72-; W. Rassman et.al., Journal of Thoracic and Cardiovascular Surgery, 1968, Vol. 56, No. 6, p. 858-; David Goldfarb, Prog. Cardiovasc. Dis., 1969, Vol. 12, No. 3, p. 221-; W. J. Kolff, Progress in Cardiovascular Diseases, 1969, Vol. XII, No. 3 page 243; Peter Schiff et.al., Trans. Amer. Soc. Artif. Int. Organs Vol. XV, 1969, p. 424-; and, Mark P. Anstadt et.al., Chest, 1991, Vol. 100, p. 86-; furthermore, an apparatus able to synchronize expansion and contraction of said membrane member with heart beat is disclosed in the reports of W. Rassman et. al. and Peter Schiff et.al. described above).

However, since these apparatuses involve the containment of both ventricles within a vessel for their application, they inevitably require both thoracotomy and incision of the pericardium, thus placing a considerable burden on patients. Consequently, they are not suitable for the purpose of routine cardiac assistance (assistance of cardiac contraction).

3) Non-Thoracotomy Types

In order to solve the above-mentioned problems of the prior art, an apparatus has been reported in which a vest-like air bladder is mounted on the chest to cyclically change the internal pressure of the thoracic cavity by compressing and releasing the thorax as a result of inflating and deflating said air bladder by the feeding and discharge of air into said air bladder (refer to Henry R. Halperin et.al., IEEE Transactions on Biomedical Engineering, 1987, Vol. BME-34, No. 9, p. 738-).

However, although this apparatus compresses the heart, since this force is transmitted from the thorax to the thoracic cavity and finally to the pericardium, force is required to oppose the resistance of each of the force transmitting sites in order to obtain reliable effects (assistance of cardiac contraction). In addition to the size of the gas feeding device being considerably large, compression of the thorax places a burden on patients (in terms of breathing effort in opposition to said compression as well as pain).

DISCLOSURE OF THE INVENTION

Inventors of the present invention have earnestly studied to solve the above-mentioned problems of the prior art, namely to provide an internal cardiac assist apparatus that (1) is less burden on patients (by not requiring thoracotomy or incision of the pericardium, having little effect on breathing and causing little pain), (2) does not require to equip a complicated gas feeding device, and (3) is able to reliably assist the cardiac contraction over a long period of time.

As a result of the above efforts, it was discovered that the above-mentioned problems could be solved by accurately inserting a balloon at a location inside the body so that said balloon makes contact with the pericardium at a site that corresponds, in terms of location, with the ventricles between the anterior chest wall and the pericardium during the process of inflating said balloon, thus leading to the present invention.

Namely, the apparatus of the present invention is an internal cardiac assist apparatus comprising: a balloon having variable internal volume; and, a tube that feeds and discharges a gas within said balloon, one end of which is sealed; wherein said balloon being secured to said tube so that said balloon contains said tube for a prescribed length near said one end of said tube therein and moreover at least one hole for feeding and discharge of said gas being opened in the lengthwise direction in the wall of the portion of said tube contained in said balloon.

Here, the lateral cross-section of the above-mentioned balloon during inflation thereof is in the shape of a tongue, and moreover, at least the ends on both sides of the portion corresponding to the base of that tongue are secured to the above-mentioned tube.

In addition, the lateral surface of the above-mentioned balloon during inflation thereof may be nearly in the shape of a rectangle, with the shapes of the upper and lower surfaces being oval. Said balloon also may have at least one hypothetical surface between the upper and lower surfaces that has a surface area smaller than the surface area of said upper and lower surfaces.

Moreover, the above-mentioned balloon may be engaged with the inner wall of the above-mentioned tube at its base, may be contained in the internal space of said tube during deflation of said balloon, and may burst outside said tube during inflation of said balloon.

Furthermore, although a single tube for both feeding and discharge of gas is normally used for the above-mentioned tube, a duplex tube, in which concentric tubes are separately used for feeding and discharge, or a single tube having an internal septum, wherein the internal chambers formed by said septum are respectively used for feeding and discharge, may also be used. In addition, said tube may be provided with at least one each of holes for the above-mentioned feeding and discharge, respectively, in the lengthwise direction of said tube so as to connect each tube or each internal chamber (with respect to the shape of said tube, it is preferable that the cross-sectional shape be such that at least the region that makes contact with the incision in the skin when the present apparatus is inserted in the body is in the shape of an oval).

Moreover, a hole may be provided in the above-mentioned one sealed end of the tube that passes radially through said tube.

In addition, an internal cardiac assist apparatus comprising: a balloon having a variable internal volume; and a single tube consisting of two proximal and parallel straight tube portions for feeding or discharge of gas into said balloon or a single straight tube portion and a ring-shaped curved tube portion having end(s) that is/are connected to the end(s) of said straight tube portion(s); wherein said balloon being secured to said tube so that it contains the curved tube portion of said tube, and moreover at least one each of holes for feeding and discharge of said gas being opened in the wall of the curved tube portion of said tube, can also be used for the apparatus of the present invention.

Here, the lateral surface of the above-mentioned balloon during inflation thereof may be in the shape of a tongue, or the lateral surface during inflation thereof may be nearly in the shape of a rectangle, the upper and lower surfaces forming a flat surface, and having at least one hypothetical surface between the upper and lower surfaces that has a surface area smaller than the surface area of said upper and lower surfaces.

Moreover, a tab may be provided on the wall of the curved tube portion of the above-mentioned tube, and a through hole may be opened in that tab.

In addition, in addition to the above-mentioned apparatus, a device that detects heart beat, and a control device that performs the above-mentioned feeding and discharge of gas synchronous with the detected heart beat may also be equipped.

Moreover, the above-mentioned device that detects heart beat may include a first electrode and a second electrode, with said first electrode attached at the region on the opposite side of the direction of balloon inflation or end of said tube, and said second electrode being a ring-shaped electrode made of silver or containing a silver compound arranged to be able to slide on the outer surface of said tube.

DETAILED DESCRIPTION

Figure 1:
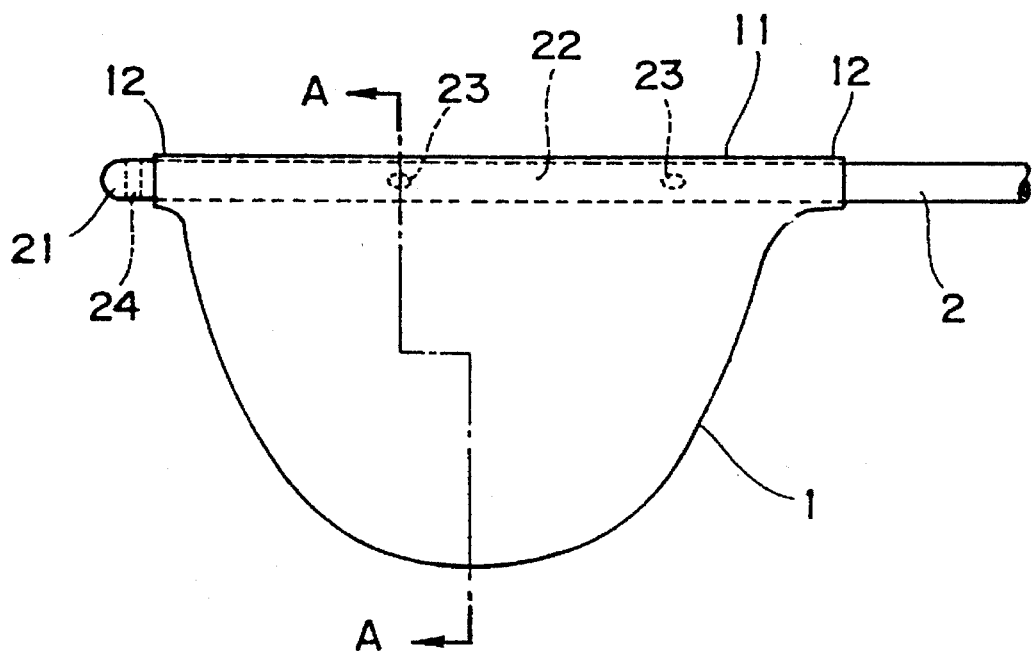
FIG. 1 is a side view (during balloon inflation) that schematically illustrates one embodiment of the apparatus of the present invention.

The following provides a detailed explanation of the present invention while referring to the attached drawings. The apparatus shown in the drawings (refer to FIG. 1 and FIG. 2) has for its basic constituents balloon 1, the internal volume of which changes corresponding to the inflow and outflow of gas, tube 2, the end 4 of which is sealed, which feeds and discharges a gas (that is both non-corrosive and non-inflammable, preferably has a low molecular weight to minimize resistance of flow, and for which helium is used optimally, but air may also be used in consideration of costs) inside said balloon.

Here, in consideration of the present apparatus being used by being inserted and arranged in the body for a long period of time, it is preferable that the material of balloon 1 have a low level of reactivity with the living body as well as be able to withstand repeated inflation and deflation of said balloon. Typical examples of these materials include natural rubber and silicone rubber (single materials: since the material itself has considerable elasticity, although gas feeding pressure is required to overcome the resiliency of the material during inflation or inflation requires a long time in balloons using these materials, conversely, in addition to offering the advantage of a short deflation time during deflation of said balloon, the internal volume of the balloon in the deflated state is small, thus minimizing the range of the incision in the skin at the time of insertion of the present apparatus in the body); polyvinyl chloride (single material: since the elasticity of the material itself is not as great as the materials described above, in the case of balloon using this material, said balloon is inserted into the body either folded in the manner of a paper balloon or wrapped around tube 2); and polyurethane coated onto a woven fabric of synthetic fiber such as nylon (composite material: since the elasticity of balloon using this material is also not as great as the previously described materials, said balloon is inserted into the body in the same manner as the one made of polyvinyl chloride). On the other hand, since the material used for tube 2 also is required to have low reactivity with the living body in the same manner as the balloon, typical examples of these materials include medical metal materials such as stainless steel and polymer materials such as polyvinyl chloride and so on that have low reactivity with the living body as well as rigidity (those that do not bend easily and do not have excessive plasticity in the manner of rubber tubes; since the present apparatus is inserted into the body from the outside without requiring the chest to be opened as a general rule, those materials that do not have a certain degree of rigidity obstruct proper insertion and arrangement at the desired site in the body).

In addition, balloon 1 is secured to tube 2 so as to contain said tube 2 for a prescribed length near the end 21 of said tube therein. (The shape of said balloon is such that the lateral surface is in the shape of a tongue when inflated and preferably, is of a shape that has the largest inflated portion in the direction opposite from said end of said tube. This is to effectively bring said largest inflated portion into contact with the pericardium at a site that corresponds, in terms of location, with the ventricles at the time of an application of the present apparatus.) Moreover, at least the ends of both, sides 12 of the portion 11 corresponding to the base of that tongue are preferably secured to said tube (in the case there are few secured locations, it is preferable to line the non-secured portion of portion 11 with nylon woven cloth and so forth). This is to restrict the direction of inflation of balloon 1 to the direction that results in compression of the ventricles when a gas has been fed into the inner space after insertion of the present apparatus into the body. As a result, force is effectively transmitted to the ventricles (via the pericardium) accompanying inflation of said balloon.) Moreover, at least one hole 23 for feeding and discharge of gas is opened in the lengthwise direction in wall 22 of the portion of said tube contained in said balloon. (Although there are two holes 23 in the embodiment shown in FIG. 2, the number of holes should be suitably determined taking into consideration the volume of balloon 1 (as a general rule, several types are prepared according to the body weight of the patient in which the apparatus is to be used) and hole diameter. In addition, the arrangement of those holes should also be suitably determined. For example, the holes may be mutually opposed in the cross-section in the radial direction of tube 2 (the minimum number of holes in this embodiment is two; refer to FIG. 3), or the holes may be arranged so that the angles formed by the axial lines of said holes in the same cross-section are 60–90 degrees, respectively (in this state, the minimum number of holes is 3; refer to FIG. This is to facilitate smooth feeding and discharge of gas into the inner space of said balloon. Furthermore, the shape of hole 23 is not limited to a round hole, but may also be in the shape of, for example, a long hole or slit.)

Figure 5:
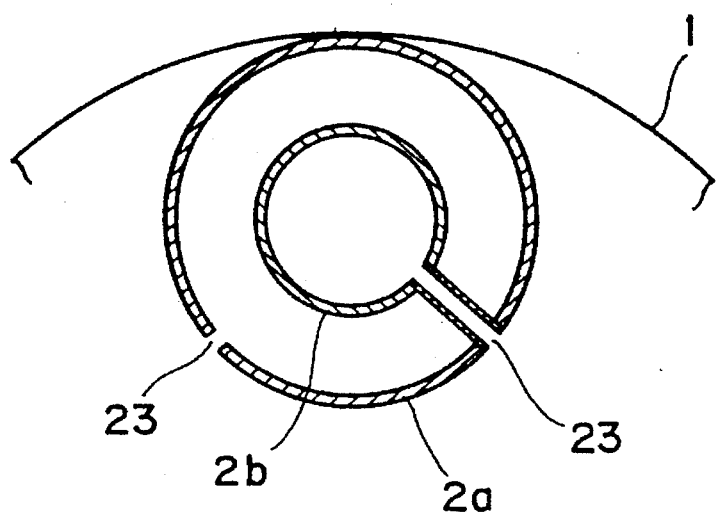
FIG. 5 is an enlarged view of the main part corresponding to FIG. 2 that shows a different embodiment of the tube.
Figure 6:
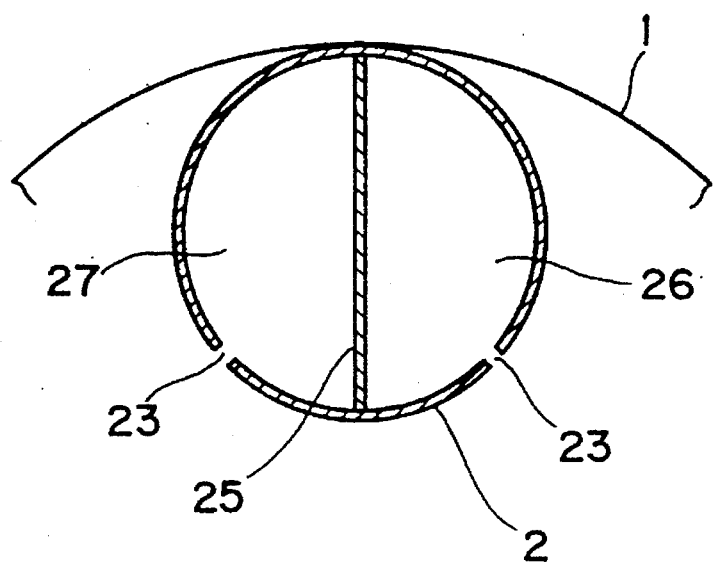
FIG. 6 is an enlarged view of the main part corresponding to FIG. 2 that shows another different embodiment of the tube.

In addition, although the above-mentioned tube is a single tube used for both feeding and discharge, as shown in FIGS. 5 and 6, the above-mentioned tube may be a concentric duplex tube 2a,2b in which the above-mentioned tube is divided into a feed portion and discharge portion, or a single tube having an internal septum 25 wherein internal chambers 26 and 27 formed by said septum are respectively used for feeding and discharge. By then providing at least one each of the above-mentioned feeding and discharge holes 23 for feeding and discharge, respectively, in the lengthwise direction of tube 2 so that each of the tubes or internal chambers are connected thereto, feeding and discharge of gas to the space inside balloon 1 can be performed more smoothly (Separation of the gas flow paths allows the resistance caused by back flow of the gas within the tubes and holes 23 when changing from feeding to discharge to be decreased. In addition, in the tubes of this embodiment, it is preferable to arrange the holes for feeding and discharge so that they are each arranged in a row in the lengthwise direction and one row of holes and another row of holes forms an angle of 90–120 degrees in the cross-section in the radial direction of said tubes. This is done to minimize the resistance caused by disturbance of gas flow inside the balloon since the flow of gas inside the balloon is nearly in the same direction when changing from feeding to discharge. Furthermore, the shape of holes 23 is the same as that described above.)

Furthermore, although all of the cross-sections of the tubes that have been illustrated thus far have been circular, it is preferable that at least the region that makes contact with the incision in the skin at the time of insertion of the present apparatus into the body is in the shape of an oval. Since the skin incision is made linearly, as a result of the above-mentioned region having an oval shape, said tube and said incision in the skin are more anatomically compatible, thus reducing the effects on the tissue in contact with said tube. More preferably, the cross-sections of those portions anterior to the above-mentioned region that makes contact with the skin incision should all have oval shapes. Since the above-mentioned region that makes contact with the skin incision varies according to the patient in which the present apparatus is to be applied, a passive reason for providing an oval shape over a considerably broad range in the lengthwise direction of said tube is to give the present apparatus universality. Conversely, an aggressive reason would be to inhibit axial rotation of the tube when the present apparatus is inserted in the body.

Moreover, hole 24 may be provided in sealed end 21 of tube 2 that passes radially through said tube. Although the present apparatus is based on not requiring the chest to be opened, when used as a cardiac assist apparatus in the case of the chest having been opened for other purpose, for example, after performing heart surgery, this hole 24 is provided to allow surgical thread to be passed through it to secure the present apparatus so that it is not shifted from its prescribed location in the body (the present apparatus is secured to a rib).

Figure 7:
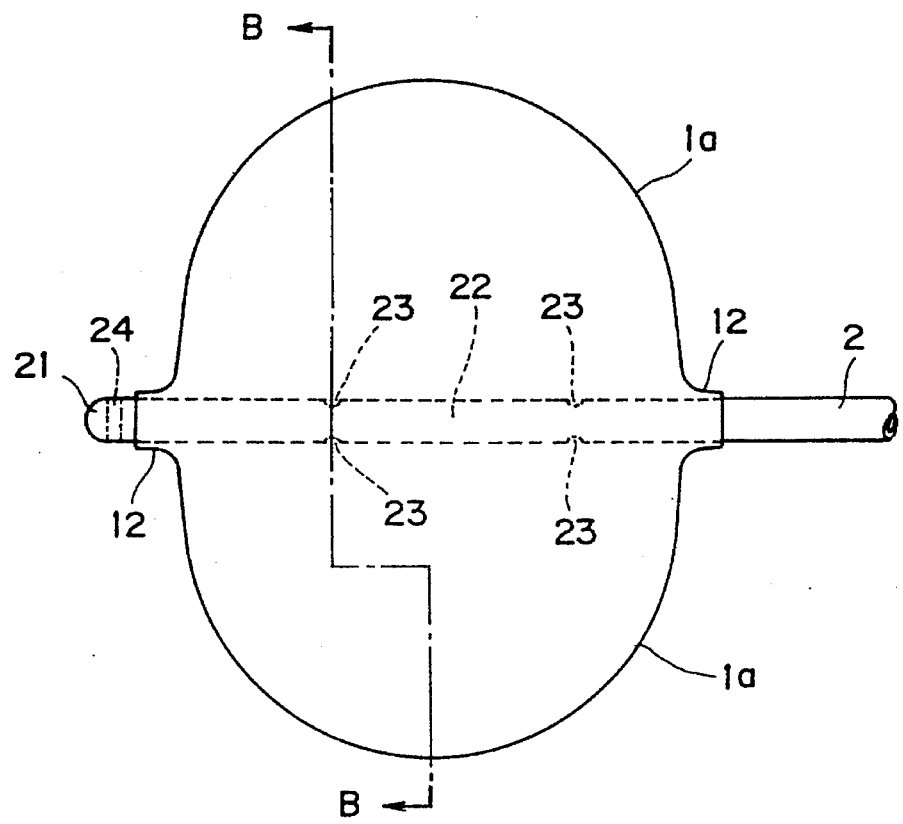
FIG. 7 is a side view (during balloon inflation) that schematically illustrates a different embodiment of the apparatus of the present invention.
Figure 8:
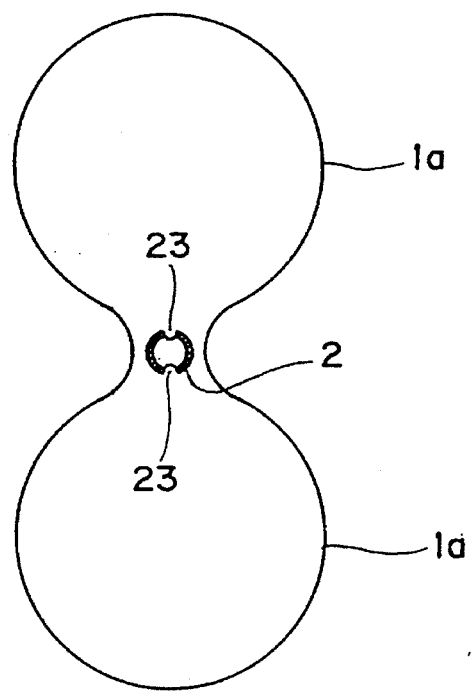
FIG. 8 is a cross-sectional view taken along line B—B of FIG. 7.

Furthermore, although the direction of inflation of balloon 1 explained thus far has restricted to one direction, depending on the particular case, it may also be given a shape (1a) so that there is a balloon of the same shape in the upper portion of the drawing as shown in FIG. 7. (In the case of a balloon of this shape, the upper and lower (refer to FIG. 8) balloons are formed into a single unit, with gas mutually passing between those internal spaces. Furthermore, said balloon 1a is secured to tube 2 at at least site 12, while the other portion that is not secured is lined with nylon woven fabric and so forth.) Since the use of a balloon of this shape eliminates the need for precise adjustment or confirming steps of angle (around an axis of tube 2) at the time of insertion of the present apparatus into the body, it is advantageous in emergency situations.

Figure 9:
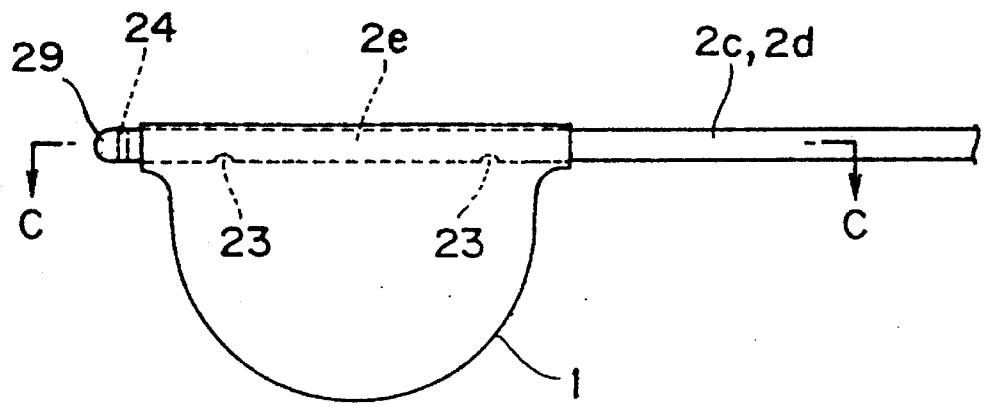
FIG. 9 is a side view (during balloon inflation) that schematically illustrates another different embodiment of the apparatus of the present invention.
Figure 10:
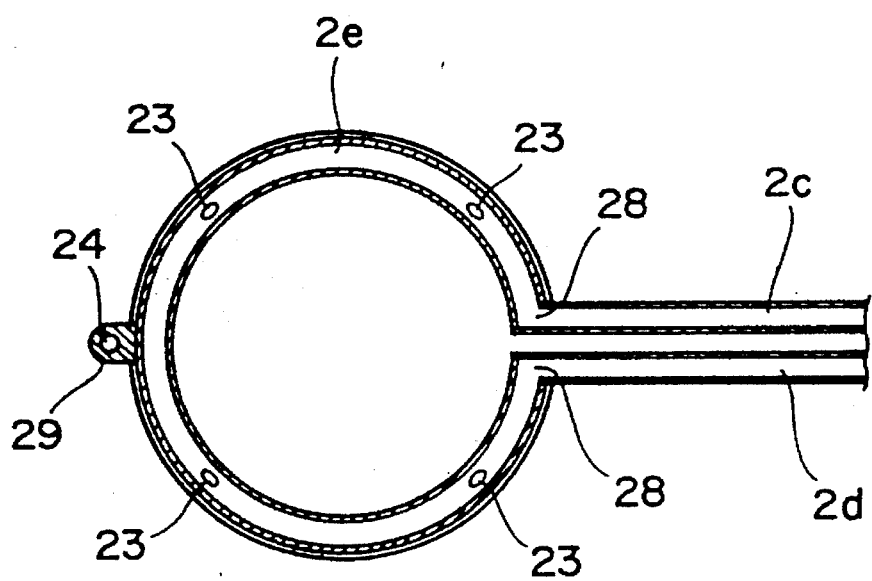
FIG. 10 is a cross-sectional view taken along line C—C of FIG. 9.

Moreover, an apparatus having for its basic constituents balloon 1, having a variable internal volume, and a single tube consisting of two proximal and parallel straight tube portions 2c and 2d for feeding and discharge of gas, respectively, into said balloon, and a ring-shaped curved tube portion 2e having ends 28 that respectively connects each end of said straight tube portions as shown in FIGS. 9 and 10, wherein said balloon being secured to said tube so as to contain said curved tube portion therein, and moreover at least one each of holes 23 for feeding and discharge of said gas is opened in the wall of the curved tube portion of said tube, can also be used for the apparatus of the present invention. (In the case of an apparatus of this embodiment, since said curved tube portion spatially forms a flat surface, said flat surface serves as a guide. As a result, the insertion of the present apparatus into the body at the prescribed location is able to be performed smoothly, and moreover axial rotation of the straight tube portion is inhibited, thus allowing the present apparatus to be used safely for a long period of time without imposing a burden (such as pain and so forth) on the patient. Furthermore, in the drawings (refer to FIG. 10), although two each of holes 23 for feeding or discharge are provided in the upper half or lower half of curved tube portion 2e in FIG. 10 on the feeding side, and in the upper half or lower half of curved tube portion 2e in FIG. 10 on the discharge side, the number, shape and arrangement of said holes can be suitably selected in the same manner as the previously described embodiments of the present invention.) In addition, in the drawings (refer to FIG. 10), although the feeding side pathway and discharge side pathway of the curved tube portion 2e are connected (in this embodiment, since the connections between each of the straight tube portions and gas feeding and discharging means can be made independently and further the feeding and discharge of gas are not performed simultaneously, this is not particularly disadvantageous.), a plug may be separately inserted at an intermediate position of said curved tube portions. Moreover, for the same reason, straight tube portions 2c and 2d may be in the form of a single tube. Here, the lateral surface of the above-mentioned balloon is in the shape of a tongue when it is inflated. (In this case, it is preferable to line the portion not secured on the opposite side of the inflating side of said balloon with nylon woven fabric and so forth in the same manner as the embodiment described above. Furthermore, the reasons for selection of this shape and for lining are the same as in the previously described embodiments.) Furthermore, in the case of using the present apparatus by securing inside the body, a tab 29 is provided at a suitable position on the wall of curved tube portion 2e, and preferably at the foremost end of said curved tube portion, namely the location farthest away from end 28, and through hole 24 is then opened in said tab 29 in the same manner as in the previously described embodiments.

Figure 11:
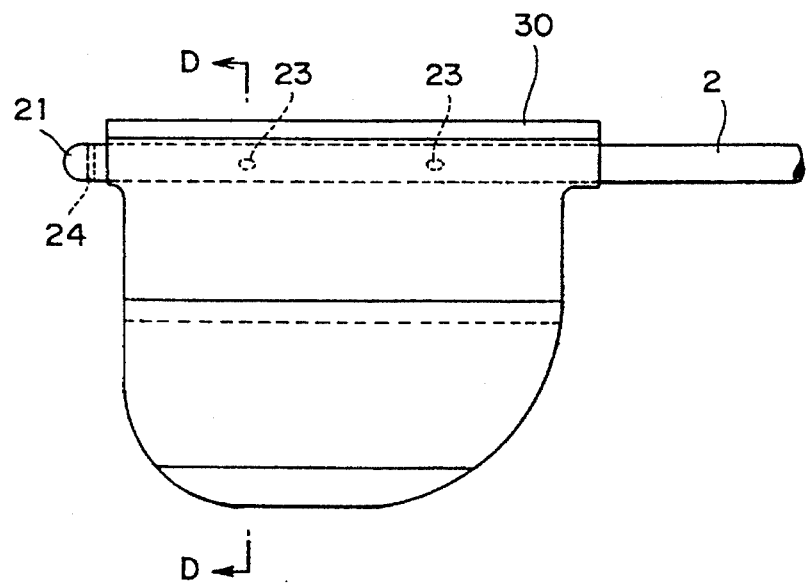
FIG. 11 is a side view (during balloon inflation) that schematically illustrates another different embodiment of the apparatus of the present invention.
Figure 12:
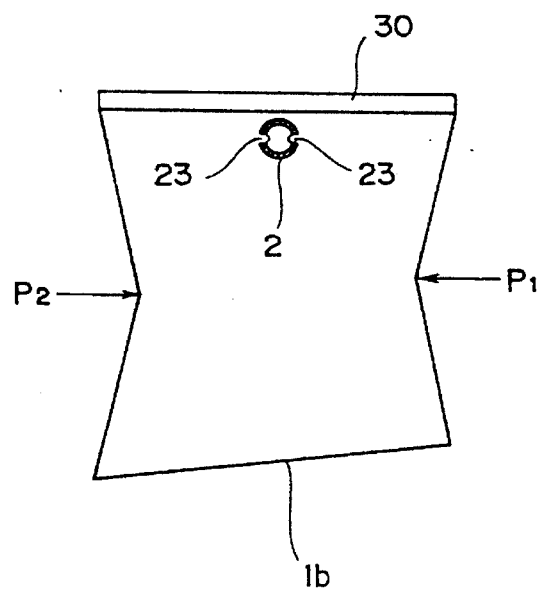
FIG. 12 is a cross-sectional view taken along line D—D of FIG. 11.

In the balloons explained thus far, although the direction of inflation has been restricted to a single direction (refer to FIGS. 1 and 9) or two directions (refer to FIG. 7), and the shape of said balloon within a surface perpendicular to the tube during inflation of said balloon is nearly circular (one device in FIG. 1, and two devices in FIG. 9) or semi-circular (refer to FIG. 7), as shown in Figs. 11 and 12, the present apparatus may also be that in which the lateral surface during inflation of said balloon is nearly rectangular in shape, the shape of the upper and lower surfaces is oval, and there is a hypothetical surface between said upper and lower surfaces having a surface area smaller than that of said upper and lower surfaces. (in the case of an apparatus of this embodiment, the bottom surface of balloon 1b (the surface that makes contact with the heart) is flat, and coupled with the pliancy of the material of said balloon (the same as the other embodiments described above), demonstrates a good fit with the shape of the heart surface. Furthermore, said balloon demonstrates so-called bellows motion in which, points P1 and P2 shown in FIG. 12 as well as the upper and lower surfaces make contact with each other during deflation.)

Here, a cord-like object that passes through points P1 and P2 in FIG. 12 (this merely indicates an example and does not impair the use of a multiple number of points P1 and P2 in which there is the same number of points P1 and P2 in the vertical direction) is wound at least once over the outer surface of balloon 1b so that said points P1 and P2 do not jump outwards during inflation of said balloon, or in other words, so that the shape of FIG. 12 is maintained. (Said cord-like object is secured to one of either the left or right surfaces. Furthermore, the above-mentioned "hypothetical surface" refers to the surface that is formed with this wound cord-like object during expansion of said balloon.) Moreover, the lengths of the left and right surfaces are different (in FIG. 12, the length of the left side is longer than that of the right side). This being the case, the upper and lower surfaces during inflation of balloon 1b (the lower surface is lowered to the left in FIG. 12) are not parallel, thus allowing pressure to be selectively applied to the ventricle, the target of application of the present apparatus (left side of the lower surface in FIG. 12; the atrium is located at the right side of the lower surface). In particular, a balloon of this embodiment is advantageous since there are no restrictions on the position of the patient. (The position of heart in the body may change depending on the position of the patient. For example, although this shift in position is mild in the supine position, since the heart moves downward in the direction of the left chest due to its own weight in the lateral position, particularly in the left lateral position, the heart moves in the direction of the left chest, in the case of the balloons of the embodiments shown in FIG. 1, FIG. 7 and FIG. 9, it becomes difficult to accurately bring the apex (largest portion during inflation) of said balloon in contact with the ventricle (which results in the patient being forced to remain in the supine position). However, in the case of the balloon of this embodiment, once the balloon is brought in contact with the ventricle, since said balloon is able to follow any shifts in position of the heart even if the patient changes his or her position also causing the heart to change its position, the burden on the patient can be alleviated.) Furthermore, in this embodiment shown in the drawings, both the upper and lower surfaces are oval (in the case of using the tubes (2) of the embodiments shown in FIGS. 3 through 6, while on the other hand, in the case of using the tube 2 of the embodiment shown in FIG. 10, the upper and lower surfaces are circular having a diameter nearly equal to ring-shaped curved tube portion 2e).

Moreover, cushion member 30 is preferably additionally provided on the upper surface. This cushion member 30 is provided to alleviate the burden (sensation of pressure on the chest wall accompanying inflation and deflation of the balloon) on the patient during use of the present apparatus. An independent bladder from the balloon may be used for this cushion member 30. (This cushion member 30 should be in the deflated state when the present apparatus is inserted into the body, and then once arranged at the prescribed location in the body, should be inflated. However, this cushion member 30 requires a supply route for the activating medium that is separate from tube 2.) Alternatively, a plastic air sheet or polyurethane sheet may be affixed to the upper surface as said cushion member 30. In either case, this cushion member 30 should have the function of a cushion, have low reactivity with the living body, have durability equal to that of the balloon and be able to be folded up.

Figure 13:
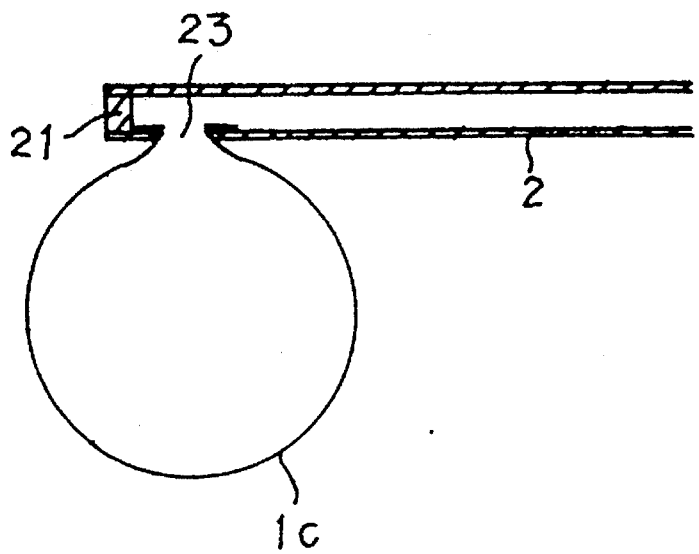
FIG. 13 is a lateral cross-sectional view (during balloon inflation) that schematically illustrates another different embodiment of the apparatus of the present invention.
Figure 14:
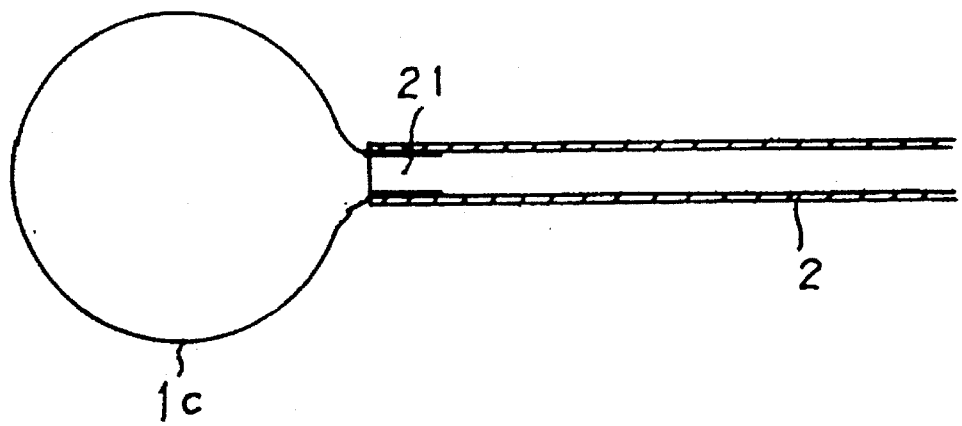
FIG. 14 is a lateral cross-sectional view (during balloon inflation) that schematically illustrates another different embodiment of the apparatus of the present invention.

In the balloons that have been explained thus far, although balloons 1, 1a and 1b are arranged outside tube 2, the present apparatus may be that in which said balloon is contained in the inner space of said tube during deflation of said balloon and then burst outside the tube during inflation (refer to FIGS. 13 and 14). This is to facilitate smooth insertion and removal of the present apparatus from the body. In these embodiments, the base of said balloon engages with the inner wall of said tube, and is, for example, attached to the inner wall of said tube. In addition, containment of said balloon can be performed by, for example, creating negative pressure inside said tube. Furthermore, together with the above-mentioned holes 23 or the above-mentioned end 21 of said tube (that is open) being feeding and discharge openings for a gas into the inner space of said balloon 1c, in this example, they also serve as the opening from which said contained balloon bursts out.

Figure 15:
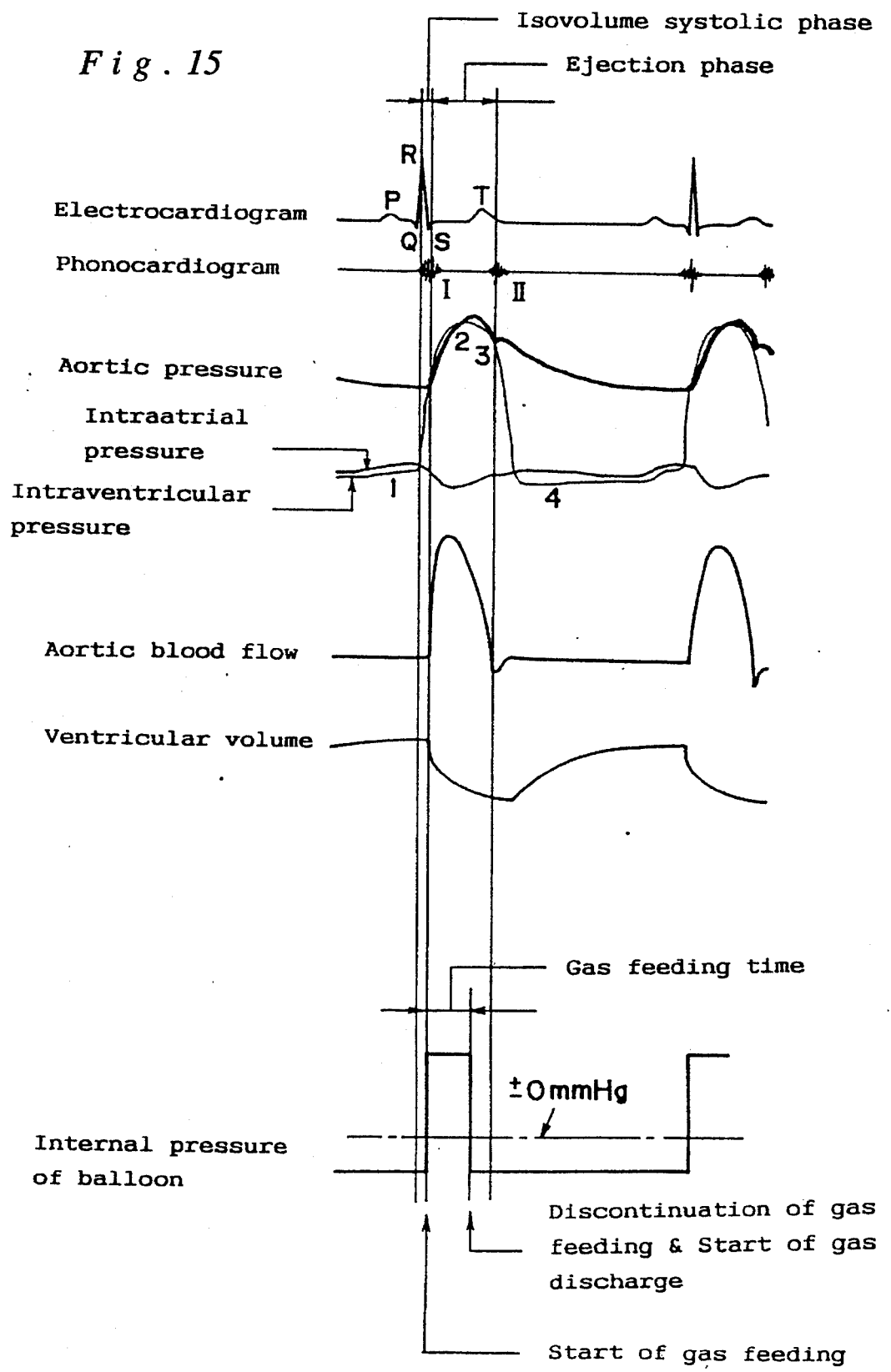
FIG. 15 is a schematic view of the timing of feeding and discharge of gas into balloon (1).

The following provides an explanation of the action of the present apparatus based on FIG. 15. (The drawing shows one cycle of the left heart system of the heart. Furthermore, the timing at which feeding and discharge of gas are performed to balloon 1 of the apparatus of the present invention is added at the bottom of this drawing.)

First, an explanation is provided regarding the pumping function of the heart (source: Encyclopedia of Medical Science, 25, p. 74–75).

To begin with, atrial excitation that begins in the sinoatrial node results in elevation of left atrial pressure (point 1 in the drawing). Left intraventricular pressure rises slightly as blood flows in. Next, the QRS wave appears on electrocardiogram as a result of atrioventricular conductivity occurring with a constant delay. Simultaneous to the appearance of the QRS wave, contraction of the left ventricle begins followed by a rapid increase in intraventricular pressure. At the point this pressure exceeds intraatrial pressure, the mitral valve closes and the first sound (I) is recorded on a phonocardiogram. The amount of time required until intraventricular pressure reaches aortic pressure is referred to as the isovolume Systolic phase, and the aortic valve opens close to the time this phase is completed. Time 2 in the previous drawing is referred to as the ejection phase. Aortic blood flow demonstrates a peak as shown in the drawing, with roughly 70 ml being ejected during a single contraction. When ejection of blood stops and the ventricle relaxes, the aortic valve closes due to back flow of blood in the aorta and the secondary sound (II) is recorded on the phonocardiogram. Moreover, incisura appear in the aortic pressure wave (point 3 in the drawing). After an extremely short isovolume diastolic phase after the recording of the secondary sound (II), blood flow into the: ventricle continues during the time intraatrial pressure exceeds intraventricular pressure (time 4 in the drawing). Ventricular volume reaches 120–130 ml at the end of the diastolic phase. Contraction and expansion of the right heart system is basically the same as that of the left heart system. In the case of the normal heart, the entire systolic phase from the start of the Q wave on electrocardiogram to completion of closing of the aortic valve (generally referred to as the systolic phase) is considered to last roughly 0.37 seconds at a heart rate of 70 beats/min. On the other hand, since the contracting strength of cardiac muscle of cardiac failure patients is weak in comparison with that of healthy subjects, the rate of ejection of blood is typically slower, thus being unable to obtain adequate circulation of blood.

The apparatus of the present invention allows the cardiac output to approach than of a normal heart using the effects of increased blood flow by enhancing the contracting strength of cardiac muscle. More specifically, a small incision is made in the skin near the processus xiphoideus to an extent that allows insertion of tube 2, 2a and 2b or 2c, 2d and 2e containing balloon 1 in the deflated state. The present apparatus is then inserted and arranged at the trigonum pericardiacum in the absence of the pleura between the anterior chest wall and pericardium in such a manner that ventricle exists in the direction of inflation of said balloon. A gas is fed into the inner space of said balloon by a feeding device (not shown; composed of a compressor and accumulator as a general rule) roughly at the time of opening of the aortic valve. Said balloon is thus inflated resulting in the ventricle being compressed for a prescribed period of time (we believe that it is not necessary to inflate said balloon throughout the entire ejection phase, but at least until intraventricular pressure nearly reaches its peak value).

On the other hand, since cardiac assistance by this balloon 1 is not required during the diastolic phase of the heart (and is on the contrary, detrimental), it is necessary that the balloon be able to be promptly deflated by the end of the systolic phase of the heart. More specifically, together with the feeding of gas to balloon 1 being discontinued, gas is forcibly discharged from said inner space. (The device for accomplishing this is located outside the body. Namely, a three-way valve (with the three valve ports connected to the gas feeding means, gas discharging means and tube 2, respectively) is provided at a suitable location on a means for connecting tube 2 to the gas feeding means. The gas flow path within this valve should be switched so that the gas flows from the gas feeding means to tube 2 or from tube 2 to the gas discharging means. Naturally, the type of this valve as well as its quantity are not restricted to that described above. For example, in the embodiment in which gas feeding and discharging are separated as shown in FIGS. 9 and 10, shutoff valves may be provided independently at suitable locations of a means for connecting the gas feeding side to the gas feeding means as well as a means for connecting the gas discharging side to the gas discharging means. The timing of opening and closing of those valves may then be controlled with a control device.)

The contraction of the heart is then assisted by the cyclical repetition of inflation and deflation of this balloon 1.

Furthermore, the period of inflation and deflation of balloon 1 is generally synchronized with the heart beat of the heart to be assisted. In order to realize this, in addition to the devices described above (tube, balloon and gas feeding and discharging means), a device that detects heart beat, and a device that feeds and discharges gas to balloon 1 synchronous to the detected heart beat, should be equipped.

An electrocardiograph can be used for the heart beat detection device, while an ordinary industrial synchronized control device can be used for the heart beat synchronized control device. Naturally, the present invention is not limited to these devices, but rather, any such devices may be used provided they are equipped with a function that allows heart beat to be detected accurately and transmission of detected signals without delay to a heart beat synchronized control device, and a function that performs switching of the above-mentioned valve at a prescribed periodic time (if necessary, a control of the amount of gas feeded too) according to said detected signals, respectively. (Feeding of gas is started after waiting for an arbitrary delay (scores of miliseconds to a few hundred of miliseconds) following confirmation of the start of the systolic phase of the heart by the heart beat synchronized control device resulting from detection of the R wave of the electrocardiogram (this is an established technique using, for example, a pacemaker). Gas feeding time and gas feeding pressure are suitably set to match individual differences (cardiac muscle contraction rate and blood pressure) of the patient in which the apparatus is to be applied.)

Figure 16:
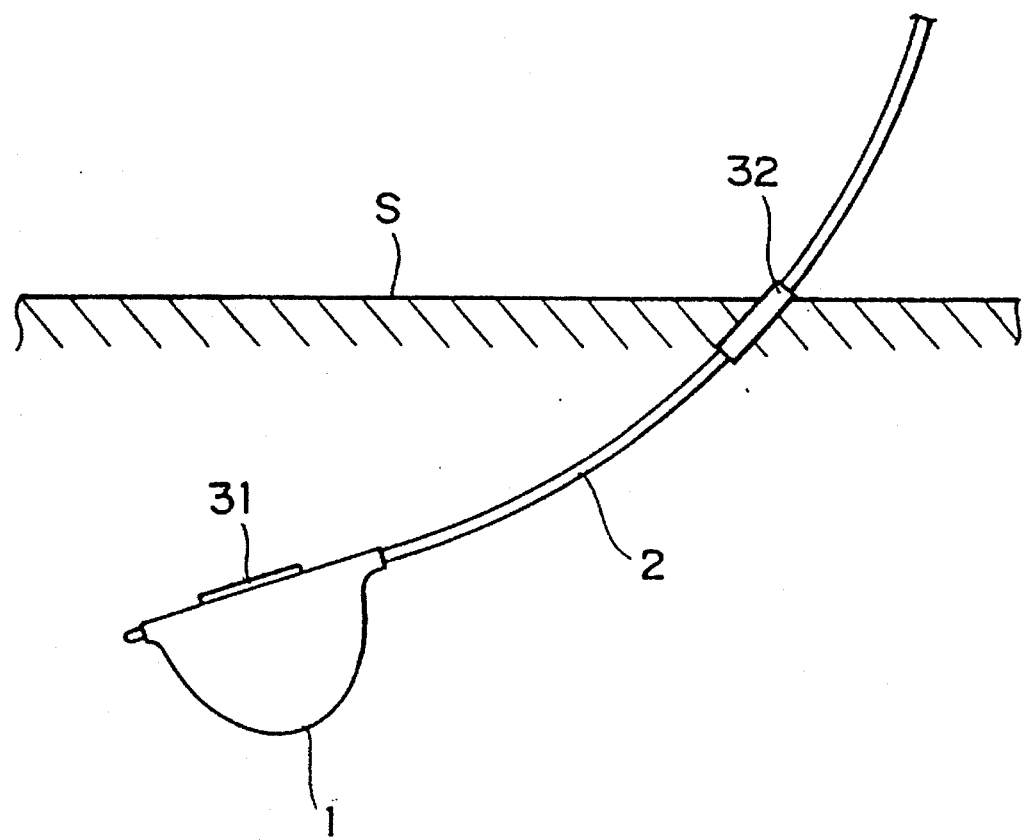
FIG. 16 is a schematic view of the mode of arrangement of electrodes of a device that detects heart beat additionally provided in the apparatus of the present invention.

Here, the above-mentioned device that detects heart beat may include a first electrode 31 and a second electrode 32. Said first electrode may be attached at the region on the opposite side of the direction of balloon inflation or end of the tube, while said second electrode may be a ring-shaped electrode made of silver or containing a silver compound arranged to be able to slide on the outside of said tube. (Refer to FIG. 16. In this embodiment, the location where said first electrode is arranged is the region of the tube on the opposite side of the direction of balloon inflation.) In order to apply the internal cardiac assist apparatus of the present invention to match patient status, a device for detecting heart beat is indispensable. This being the case, tube 2, which is inevitably located near the heart, should be effectively used as the location where the first and second electrodes are arranged. Since the balloon is normally inserted to a depth of scores of centimeters from the incision in the skin, this is suitable as the interval between electrodes. Since the use of the present apparatus for a long period of time is naturally taken into consideration when selecting the materials that compose the electrodes, those materials having low reactivity with the living body are used. Materials that are used preferably include solid silver, silver-plated metal or a silver compound such as silver diazine chloride impregnated into a carrier. Silver is used because silver ions have antimicrobial action. The second electrode is arranged close the incision in the skin S in order to take full advantage of the antimicrobial action of silver. (Since the depth at which the balloon is inserted in the body from the incision in the skin varies depending on the patient, said second electrode is formed into a ring shape that is able to slide over the outside surface of tube 2.)

EMBODIMENTS

The apparatus of the present invention having a specification indicated below (refer to FIGS. 1 and 2) was surgically inserted and arranged between the sternum and pericardium of adult mongrel dogs having body weights of 10 kg and 13.5 kg, respectively. (The surgical procedure consisted of placing the animals in the supine position, making a midline incision to the sternum, peeling back the muscle layer of the left chest wall, removing said muscle layer from the 2nd to 7th rib including roughly the anterior ⅓ of the intercostal muscle over the width between the sternum and thoracic vertebrae, placing the present device at the prescribed location, and changing the position of the animals to the prone position. The muscle layer of the chest wall was removed for observation of status in this case.) Following this procedure, the synchronized assistance of the ventricle as well as the action to cardiac arrest were confirmed.

Figure 2:
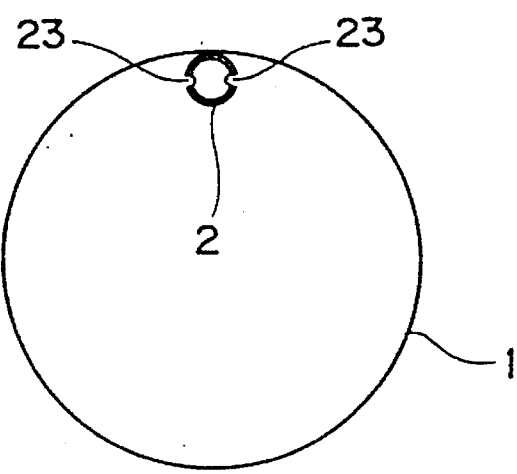
FIG. 2 is a cross-sectional view taken along line A—A of FIG. 1.
Figure 3:
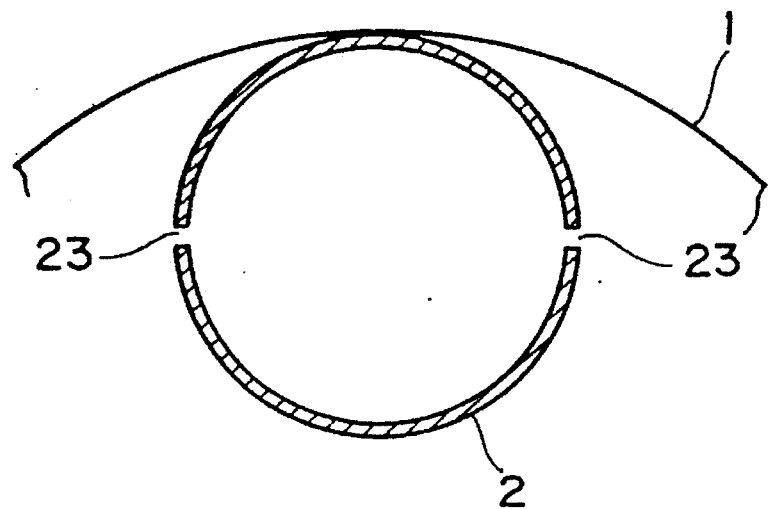
FIG. 3 is an enlarged view of the main part of FIG. 2.
Figure 4:
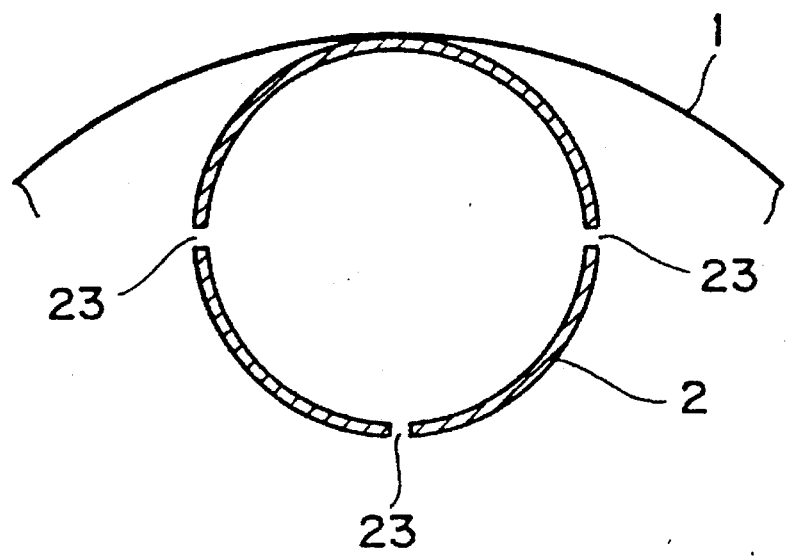
FIG. 4 is an enlarged view of the main part corresponding to FIG. 2 that shows a different embodiment of the layout of feeding and discharge holes

(1) Maximum internal volume during balloon inflation: 65 ml
(2) Tube: Simple tube having an inner diameter of 6 mm
(3) Tube length within balloon: 68 mm
(4) Balloon material: Polyurethane coating over a woven cloth of synthetic fiber
(5) Tube material: Polyvinyl chloride
(6) Holes: Minor axis 3 mm×major axis 4 mm×4 holes (the holes were arranged as shown in FIGS. 1 and 2)

Furthermore, the test conditions were as shown below.
(A) Gas feeding pressure: 150–200 mmHg
(B) Gas discharging pressure: −30 mmHg
(C) Time from start of gas feeding to completion of discharge: 0.08–0.12 sec.

As a result, average cardiac output increased by 40% and 34%, respectively, in comparison with not installing the present apparatus (unassisted). in general, the normal lower limit of the cardiac index (cardiac output per unit body surface area) in humans is considered to be 2.5 l/min/m². If the cardiac index falls below 2.0 l/min/m² despite medical treatment such as medication of cardiac diuretics and so forth, the application of various forms of mechanical cardiac assistance is considered. The experimental results indicated that the present apparatus allows improvement to a level equal to or above the abovementioned limit value even in serious cases demonstrating a cardiac index of 1.5 l/min/m², thus confirming that the present apparatus is extremely effective. Furthermore, although the present apparatus was left in the body for 12 hours (continuous cardiac assistance), there were no adverse side effects that would prohibit long-term use, such as pulmonary congestion and so forth. In addition, similar results were also obtained for the different embodiments of the present apparatus (FIGS. 9, 10, 13 and 14). Moreover, as a result of attempting to apply another different embodiment of the present apparatus (FIGS. 11 and 12) in subjects placed in various positions (initially in the prone position and then in the lateral position and again in the prone position), there were no difficulties encountered whatsoever, thus making it clear that the present apparatus can adapt to changes in body position.

In consideration of both the results of the present experiment along with those findings disclosed in the above-mentioned prior art, the present apparatus is assumed to be free of adverse side effects during long-term use.

Furthermore, following the experiment to confirm the effects of synchronized assistance of the ventricle, the subjects were forced into cardiac arrest using an electric fibrillator. When cardiac compression was performed by manual cardiac massage and using the present apparatus, it was confirmed that cardiac output of 50% was obtained in the case of using the use of the present apparatus in comparison with the cardiac output during manual cardiac massage.

Industrial Applicability

As described above, the present invention is able to provide an internal cardiac assist apparatus that (1) is less burden on serious cardiac failure patients (by not requiring thoracotomy or incision of the pericardium, having little effect on breathing and causing little pain), (2) does not require to equip a complicated gas feeding device, and (3) is able to reliably assist the cardiac contraction over a long period of time.

We claim:

1. An internal cardiac assist apparatus comprising:
   a balloon having a variable internal volume; and
   a tube coupled to said balloon for feeding and discharging a gas within said balloon, one end of said tube being sealed;
   said balloon being connected to said tube so that said balloon contains said tube in said balloon for a prescribed length of said tube near said one sealed end of said tube;
   at least one hole in said tube which extends in a lengthwise direction in a wall of the portion of said tube contained in said balloon, said at least one hole being arranged to feed and discharge gas therethrough;
   said balloon having a lateral cross-section which, during inflation thereof, is in the shape of a tongue having a base portion and ends on opposite sides of said base portion, at least said ends on both opposite sides of said base portion of the tongue being secured to said tube;
   said tube having a cross-sectional shape such that at least a region that makes contact with an incision in the skin of a patient when the internal cardiac assist apparatus is inserted into the body of the patient is in the shape of an oval;
   and wherein:
   said tube comprises a concentric duplex tube, which includes feeding and discharge portions, respectively; and
   at least one each of said at least one hole for gas feeding and discharge of gas are respectively provided in the lengthwise direction of said tube so as to connect each tube of said concentric duplex tube.

2. The apparatus according to claim 1, wherein said tube has a further hole therein that passes radially through said tube in the sealed end of said tube.

3. An internal cardiac assist apparatus comprising:
   a balloon having a variable internal volume; and
   a tube coupled to said balloon for feeding and discharging a gas within said balloon, one end of said tube being sealed;
   said balloon being connected to said tube so that said balloon contains said tube in said balloon for a prescribed length of said tube near said one sealed end of said tube;
   at least one hole in said tube which extends in a lengthwise direction in a wall of the portion of said tube contained in said balloon, said at least one hole being arranged to feed and discharge gas therethrough;
   said balloon having a lateral cross-section which, during inflation thereof, is in the shape of a tongue having a base portion and ends on opposite sides of said base portion, at least said ends on both opposite sides of said base portion of the tongue being secured to said tube;
   said tube having a cross-sectional shape such that at least a region that makes contact with an incision in the skin of a patient when the internal cardiac assist apparatus is inserted into the body of the patient is in the shape of an oval;
   and wherein:
   said tube comprises a single tube having an internal septum forming inner chambers in said single tube, said inner chambers formed by said septum being used for gas feeding and gas discharge, respectively; and
   at least one each of said at least one hole for gas feeding and discharge of gas are respectively provided in the lengthwise direction of said tube so as to connect said inner chambers.

4. The apparatus according to claim 3, wherein said tube has a further hole therein that passes radially through said tube in the sealed end of said tube.

5. An internal cardiac assist apparatus comprising:
   a balloon having a variable internal volume; and
   a tube member including:
      a first tube section comprising first and second proximal and parallel straight tube portions for feeding or discharge of gas into said balloon, said first straight tube portion being inside of said second straight tube portion; and
      a curved tube portion having at least one end which is connected to ends of said first and second straight tube portions of said first tube section;
   wherein said balloon is secured to said tube so that said curved tube portion of said tube is contained within said balloon; and
   wherein at least one each of holes for feeding or discharge of said gas are opened in a wall of said curved tube portion of said tube.

6. The apparatus according to claim 5, wherein said balloon, during inflation thereof, has a lateral surface in the shape of a tongue.

7. The apparatus according to claim 5, wherein said balloon, during inflation thereof, has a lateral surface which is nearly in the shape of a rectangle, said balloon having upper and lower surfaces which are circular in shape, and said balloon having at least one surface between said upper and lower surfaces that has a surface area smaller than a surface area of said upper and lower surfaces.

8. The apparatus according to claim 7, wherein said tube has a cross-sectional shape such that at least a region that makes contact with an incision in the skin of a patient when the internal cardiac assist apparatus is inserted into the body of the patient is in the shape of an oval.

9. The apparatus according to claim 8, further comprising a tab provided on a wall portion of said curved tube portion of said tube, and wherein a through hole is provided in said tab.

10. The apparatus according to claim 6, wherein said tube has a cross-sectional shape such that at least a region that makes contact with an incision in the skin of a patient when the internal cardiac assist apparatus is inserted into the body of the patient is in the shape of an oval.

11. The apparatus according to claim 10, further comprising a tab provided on a wall portion of said curved tube portion of said tube, and wherein a through hole is provided in said tab.

12. An internal cardiac assist apparatus comprising:
   a balloon having a variable internal volume; and
   a tube for feeding and discharging gas into said balloon, said tube having an end and an internal space;
   said balloon having a base portion which is engaged with an inner wall on the end of said tube; and
   a portion of said balloon being contained in the internal space of said tube during deflation of said balloon, and wherein said balloon bursts outside of said tube during inflation of said balloon.

13. The apparatus according to claim 12, wherein said tube has a cross-sectional shape such that at least a region that makes contact with an incision in the skin of a patient when the internal cardiac assist apparatus is inserted into the body of the patient is in the shape of an oval.

14. The apparatus according to claim 13, further comprising:
   a device that detects a heart beat; and
   a control device that performs the feeding and discharge of said gas via said tube, in synchronism with the detected heart beat.

15. The apparatus according to claim 14, wherein said device that detects a heart beat includes:
   a first electrode and a second electrode;
   said first electrode being attached at a region on an opposite side of a direction of balloon inflation or the end of said tube; and
   said second electrode being a ring-shaped electrode slidably arranged on an outer surface of said tube.

16. The apparatus according to claim 15, wherein said ring-shaped electrode is at least partially made of silver.

17. The apparatus according to claim 10, further comprising:
   a device that detects a heart beat; and
   a control device that performs the feeding and discharge of said gas via said tube, in synchronism with the detected heart beat.

18. The apparatus according to claim 17, wherein said device that detects a heart beat includes:
   a first electrode and a second electrode;
   said first electrode being attached at a region on an opposite side of a direction of balloon inflation or the end of said tube; and
   said second electrode being a ring-shaped electrode slidably arranged on an outer surface of said tube.

19. The apparatus according to claim 18, wherein said ring-shaped electrode is at least partially made of silver.

20. The apparatus according to claim 1, further comprising:
   a device that detects a heart beat; and
   a control device that performs the feeding and discharge of said gas via said tube, in synchronism with the detected heart beat.

21. The apparatus according to claim 20, wherein said device that detects a heart beat includes:
   a first electrode and a second electrode;
   said first electrode being attached at a region on an opposite side of a direction of balloon inflation or the end of said tube; and
   said second electrode being a ring-shaped electrode slidably arranged on an outer surface of said tube.

22. The apparatus according to claim 21, wherein said ring-shaped electrode is at least partially made of silver.

23. An internal cardiac assist apparatus comprising:
   a balloon having a variable internal volume; and
   a tube coupled to said balloon for feeding and discharging a gas within said balloon, one end of said tube being sealed;
   said balloon being connected to said tube so that said balloon contains said tube in said balloon for a prescribed length of said tube near said one sealed end of said tube;
   at least one hole in said tube which extends in a lengthwise direction in a wall of the portion of said tube contained in said balloon, said at least one hole being arranged to feed and discharge gas therethrough;
   said balloon having:
      a lateral surface which, during inflation thereof, is nearly in the shape of a rectangle;
      upper and lower surfaces which are in the shape of an oval; and
      at least one surface between said upper and lower surfaces that has a surface area smaller than a surface area of said upper and lower surfaces;
   said tube having a cross-sectional shape such that at least a region that makes contact with an incision in the skin of a patient when the internal cardiac assist apparatus is inserted into the body of the patient is in the shape of an oval;
   and wherein:
      said tube comprises a concentric duplex tube, which includes feeding and discharge portions, respectively; and
      at least one each of said at least one hole for gas feeding and discharge of gas are respectively provided in the lengthwise direction of said tube so as to connect each tube of said concentric duplex tube.

24. An internal cardiac assist apparatus comprising:
   a balloon having a variable internal volume; and
   a tube coupled to said balloon for feeding and discharging a gas within said balloon, one end of said tube being sealed;
   said balloon being connected to said tube so that said balloon contains said tube in said balloon for a prescribed length of said tube near said one sealed end of said tube;
   at least one hole in said tube which extends in a lengthwise direction in a wall of the portion of said tube contained in said balloon, said at least one hole being arranged to feed and discharge gas therethrough;
   said balloon having:
      a lateral surface which, during inflation of said balloon, is in the shape of a rectangle;
      upper and lower surfaces which are in the shape of an oval; and
      at least one surface between said upper and lower surfaces that has a surface area smaller than a surface area of said upper and lower surfaces;

said tube having a cross-sectional shape such that at least a region that makes contact with an incision in the skin of a patient when the internal cardiac assist apparatus is inserted into the body of the patient is in the shape of an oval;

and wherein:

said tube comprises a single tube having an internal septum forming inner chambers in said single tube, said inner chambers formed by said septum being used for gas feeding and gas discharge, respectively; and at least one each of said at least one hole for gas feeding and discharge of gas are respectively provided in the lengthwise direction of said tube so as to connect said inner chambers.

* * * * *